US007553656B2

(12) United States Patent
Gimmestad et al.

(10) Patent No.: US 7,553,656 B2
(45) Date of Patent: Jun. 30, 2009

(54) **MUTANT STRAINS OF *PSEUDOMONAS FLUORESCENS* AND VARIANTS THEREOF, METHODS FOR THEIR PRODUCTION, AND USES THEREOF IN ALGINATE PRODUCTION**

(75) Inventors: Martin Gimmestad, Trondheim (NO); Havard Sletta, Trondheim (NO); Karuna Ponniah Karunakaran, Vancouver (CA); Karianne Bakkevig, Trondheim (NO); Helga Ertesvag, Trondheim (NO); Trond Ellingsen, Ranheim (NO); Gudmund Skjak-Braek, Trondheim (NO); Svein Valla, Vikhammer (NO)

(73) Assignee: FMC Biopolymer AS, Drammen (NO)

( * ) Notice: Subject to any disclaimer, the term of this patent is extended or adjusted under 35 U.S.C. 154(b) by 0 days.

(21) Appl. No.: 10/522,510

(22) PCT Filed: Jul. 24, 2003

(86) PCT No.: PCT/NO03/00257

§ 371 (c)(1),
(2), (4) Date: Sep. 17, 2005

(87) PCT Pub. No.: WO2004/011628

PCT Pub. Date: Feb. 5, 2004

(65) Prior Publication Data

US 2006/0063237 A1 Mar. 23, 2006

(30) Foreign Application Priority Data

Jul. 26, 2002 (NO) ................................ 20023581

(51) Int. Cl.
*C12N 1/20* (2006.01)
*C12P 19/04* (2006.01)
*C12N 1/00* (2006.01)

(52) U.S. Cl. .................................. 435/252.34; 435/101
(58) Field of Classification Search ........................ None
See application file for complete search history.

(56) References Cited

U.S. PATENT DOCUMENTS

| 4,490,467 A | 12/1984 | Jarman et al. | |
|---|---|---|---|
| 2004/0014197 A1* | 1/2004 | Huisman et al. | 435/252.3 |

FOREIGN PATENT DOCUMENTS

WO  WO 94/09124  4/1994

OTHER PUBLICATIONS

Chitnis Chaitanya E. et al., "Cloning of *Pseudomonas aeruginosa* algG, which controls alginate structure," *Journal of Bacteriology*, vol. 172, No. 6, 1990, pp. 2894-2900.

Franklin Michael J. et al., "Mutant analysis and cellular localization at the AlgI, AlgJ and AlgF proteins required for O acetylation of alginate in *Pseudomonas aeruginosa*," *Journal of Bacteriology*, vol. 184, No. 11, 2002, pp. 3000-3030.

Gimmestad Martin et al., "The *Pseudomonas fluorescens* algG protein, but not its mannuronan C-5-epimerase activity, is needed for alginate polymer formation," *Journal of Bacteriology*, vol. 185, No. 12, 2003, pp. 3515-3523.

Govan J.R.W et al., "Isolation of alginate-producing mutants of *Pseudomonas fluorescens, Pseudomonas putida* and *Pseudomonas mendocina*," *Journal of General Microbiology*, vol. 125, 1981, pp. 217-220.

Morea Antonella et al.: "Characterization of algG encoding C5-epimerase in the alginate biosynthetic gene cluster of *Pseudomonas fluorescens*," *Gene*, vol. 278, 2001, pp. 107-114.

Pringle J. Howard et al., "Selection of attachment mutants during the continuous culture of *Pseudomonas fluorescens* and relationship between attachment ability and surface composition," *Journal of General Microbiology*, vol. 129, 1983, pp. 2557-2569.

Schweizer Herbert P. et al., "Cloning and nucleotide sequence of the glpD gene encoding sn-glycerol-3-phosphate dehydrogenase of *Pseudomonas aeruginosa*," *Journal of Bacteriology*, vol. 176, No. 8, 1994, pp. 2184-2193.

Database Biosis ÄOnlineÜ Fakhr M.K. et al., "Mutagenesis of a plasmid that confers constitutive alginate production to *Pseudomonas syringae*," XP002971958 Database accession No. (PREV200000305692) & Phytopathology vol. 90, No. 6, Suppl., Jun. 2000, p. 23.

Database Biosis ÄOnlineÜ Herrero Marta et al.: "A T7 RNA polymerase-based system for the construction of pseudomonas strains with phenotypes dependent on TOL-meta pathway effectors," XP002971959 Database accession No. (PREV199497073630) & Gene (Amsterdam) vol. 134, No. 1, 1993, pp. 103-106.

Database Biosis ÄOnlineÜ Douthit S.A. et al., "Identification of amino acids motifs important For epimerase activity of the *Pseudomonas aeruginosa* alginate modifying enzyme, AlgG," XP002971960 Database accession No. (PREV199598304642) & Abstracts of the General Meeting of the American Society for Microbiology vol. 101, 2001, p. 278.

Database Biosis ÄOnlineÜ Franklin M.J. et al., "IPTG-controlled expression of the alginate biosynthetic gene cluster in *Pseudomonas aeruginosa* and requirement of AlgT in high-level alginate production," XP002971961 Database accession No. (PREV199598304642) & Abstracts of the General Meeting of the American Society for Microbiology vol. 95, 1995, p. 178.

\* cited by examiner

*Primary Examiner*—Nashaat T Nashed
*Assistant Examiner*—Mohammad Younus Meah
(74) *Attorney, Agent, or Firm*—Pepper Hamilton LLP (57) ABSTRACT

It is described biologically pure bacterial cultures of mutant strains of *Pseudomonas fluorescens*, which produces large amounts of alginate. The alginate may contain a certain determined content of mannuronate and guluronate residues, possible presence and determined level of acetyl groups in the alginate, and a desired molecular weight of the alginate. Also high yielding mutants with regulation of alginate production, is described. The invention further provides methods for producing new mutant strains of *Pseudomonas fluorescens* and variants thereof, and use the resulting strains in alginate production.

18 Claims, 4 Drawing Sheets

Figure 1

Restriction map of the suicide plasmids pHE55 and pMG48.

Figure 2. Growth and alginate production in fermentation with strain Pf201.

Figure 3. ¹HNMR-spectra of alginate produced by P. fluorescens 201 and mannuronan produced by P. fluorescens 20118

Figure 4: The alginate biosynthetic operon and the upstream open reading frame from *P. fluorescens*. The cloned fragments are marked as boxes on the mapline.

Figure 5

Figure 5: Restriction map of pMC1.

MUTANT STRAINS OF *PSEUDOMONAS FLUORESCENS* AND VARIANTS THEREOF, METHODS FOR THEIR PRODUCTION, AND USES THEREOF IN ALGINATE PRODUCTION

CROSS-REFERENCE TO RELATED APPLICATIONS

This application is a national stage application of PCT International Application PCT/NO2003/000257, filed Jul. 24, 2003, which claims priority to Norwegian Patent Application 20023581, filed Jul. 26, 2002.

FIELD OF INVENTION

This invention relates to new mutant strains of *Pseudomonas fluorescens*, and variants thereof, which are capable of producing large amounts of alginate. The alginate is not only produced in large amounts, but also with a certain determined content of mannuronate and guluronate residues, possible presence and determined level of acetyl groups in the alginate, and a desired molecular weight of the alginate. Also high yielding mutants with regulation of alginate production, is described. The invention further provides methods for producing new mutant strains of *Pseudomonas fluorescens* and variants thereof, and use of the resulting strains in alginate production.

DESCRIPTION OF PRIOR ART

Several microorganisms are known to produce alginate, the most studied of the bacteria is the bacterium *Pseudomonas aeruginosa*. It is however of limited use when it comes to production of alginates for use in nutrients, or pharmaceuticals, because it is associated with primary and secondary infections in mammals or humans. Other species, which might be safer sources, do not usually produce significant amounts of alginates, or alginates of sufficient high molecular weight, and can for this reason not be used.

It is known that non-pathogenic species of *Pseudomonas* such as *P. putida, P. mendocina* and *P. fluorescens* produce exopolysaccharides similar to acetylated alginates, Govan J. R. W. et al., J. of General Microbiology (1981), 125, p. 217-220. Also Conti, E. et al., Microbiology (1994), 140, p. 1125-1132 describe production of alginates from *P. fluorescens* and *P. putida*. It is however not known any stable over-producers of alginate among these strains.

U.S. Pat. No. 4,490,467 of Kelco Biospecialties Ltd. describes polysaccharide production using novel strains of *Pseudomonas mendocina*. The strains produce good yields of the desired polysaccharide, and are relatively stable in continuous fermentation. The strains are produced by exposing a wild type culture of *P. mendocina* with carbenicillin, and mutagenize the selected resistant mucoid clones with a mutagenic agent. The most stable and hence most preferred is deposited under the no. NCIB 11687. High concentrations of alginate, approximately 20 g/l, was obtained in nitrogen-limited continuous culture with a minimal glucose medium. An alginate lyase activity was present in the cultures and resulted in a low molecular weight, low viscosity polymer with rheology similar to printing grade alginate. The degradation by the lyase enzyme was remedied with the addition of proteolytic enzyme into the medium, Hacking A. J., et al., (1983) J. Gen. Microbiol., 129, p. 3473-3480. After ten generations in continuous culture, non-mucoid variants appeared, Sengha S. S., et al., (1989) J. Gen. Microbiol., 135, p. 795-804. page 799, second paragraph.

An epimerase negative mutant of the opportunistic pathogen *P. aeruginosa* was reported by Chitnis et al. (1990) J. Bacteriol., 172, p. 2894-2900. Mucoid *P. aeruginosa* FRD1 was chemically mutagenized and mutants, which were incapable of incorporating guluronic acid (G)-residues into alginate were independently isolated. Assays using G-specific alginate lyase and $^1$H-nuclear magnetic resonance analyses showed that G-residues were absent in the alginates secreted by these mutants. Goldberg and Ohman, 1987, J. Bacteriol., 169, p. 1593-1602, produced up to 1,7 g/l alginate from FRD1 in shake flasks. As usual for spontaneous alginate-producers non-mucoid revertants arise frequently (Flynn and Ohman, 1988, J. Bacteriol., 170, p. 1452-1460).

There is therefore still a need in the market for suitable sources for reliable alginate production in large amounts. In particular there is a need for stable sources producing large amounts of high quality alginate with defined structure and desired molecular weight, and especially for a source for the production of large amounts of biologically active alginate. Furthermore there is also a need for the production of pure mannuronan, which can be subjected to in vitro epimerization in order to obtain alginates with a predetermined guluronate residue (G)-content.

SUMMARY OF THE INVENTION

The present invention provides new mutant strains of *P. fluorescens*, which are stable and produce large amounts of alginate. Some embodiments of the invention is to provide variants thereof, which produce alginates with a defined structure with regard to content of mannuronate and guluronate residues, possible presence of, and determined level of O-acetyl groups and a desired molecular weight of the alginate molecules. Also high yielding mutants with regulated alginate production, and methods for their production are described. Other aspects of the invention are; methods of producing the novel mutant strains of *P. fluorescens* including variants thereof, and uses of the resulting mutants in the production of alginates, in particular medium or large-scale fermentor production of alginates, and more particularly production of biologically active alginates, or pure mannuronan. The resulting alginates are applicable in different food and industrial products such as nutrients, animal feedings, cosmetics and pharmaceuticals, they may also constitute an intermediate product suitable for further modifications by mannuronan-C5-epimerases, for instance by the epimerases of U.S. Pat. No. 5,939,289.

DETAILED DESCRIPTION OF THE INVENTION

The present invention provides a biologically pure bacterial culture of at least one mutant strain of *P. fluorescens* wherein said strain produces large amounts of alginate. In a first aspect of the invention the said strain produces at least 10 g alginate per liter medium. In preferred embodiments the biologically pure bacterial culture of at least one mutant strain of *P. fluorescens* produces at least 10 g alginate per 40-55 g carbon source per liter medium, more preferred per 50-55 g carbon source per liter medium, and most preferred the biologically pure bacterial culture of at least one mutant strain of *P. fluorescens* produces at least 10 g alginate per 40 g carbon source per liter medium.

Pure mutant strain of *P. fluorescens* bacterium and variants thereof, covered by the invention are exemplified by mutant strains selected from the group consisting of the mutant strains Pf201, Pf2012, Pf2013, Pf20118, Pf20137, Pf20118algIJΔ, Pf 20118algFΔ, Pf20118AlgLH203R and Pf201MC. In some embodiments, the invention relates to biologically pure bacterial culture of at least one strain of *P. fluorescens* wherein the strain produces alginate with alginate production characteristics of Pf201 and variants thereof that retain such characteristics. Such "alginate production characteristics" may be one of more of the following: yield in terms of g alginate/l medium (g/l) and g alginate/g carbon source (g/g carbon source), the average molecular mass, the degree acetylation and the G-content of alginate produced.

In a second aspect the present invention comprises a pure mutant strain of *P. fluorescens* wherein the said mutant is capable of producing large amounts of an alginate consisting of mannuronate residues only. Preferred variants can be selected from the group consisting of the variant strains Pf2012, Pf2013, Pf20118, and Pf20137.

In a third aspect the present invention comprises a pure mutant strain of *P. fluorescens* wherein the said mutant is capable of producing large amounts of an alginate having a defined guluronate residue (G)-content between 0 and 30%. Such embodiments may be produced by methods of the invention by exchanging, the wild type algG gene with a mutant gene, or altering the algG gene to encode a mannuronan C-5-epimerase enzyme with lower specific activity than the wild type enzyme.

In a fourth aspect of the invention the pure mutant strain of *P. fluorescens* is capable of producing large amounts of an alginate without, or with a reduced number of O-acetyl groups. Such embodiments may be produced by deleting parts of, or all of the genes algI, algJ, and/or algF. The mutant variant strains Pf20118algIJΔ and Pf20118algFΔ are capable of producing large amounts of an alginate without, or with a reduced number of O-acetyl groups, and represents preferred embodiments of this aspect of the invention.

In a fifth aspect of the present invention the pure mutant strain of *P. fluorescens* is capable of producing large amounts of an alginate with a desired molecular weight. The molecular weight of the alginate is preferably between 50,000 and 3,000,000 Daltons. Such embodiments may be produced by exchanging the wild type algL with a mutant gene encoding an alginate lyase enzyme with lower specific activity than the wild type lyase enzyme. The pure mutant variant strain Pf20118AlgLH203R represents a preferred embodiment of the said mutant, which is capable of producing large amounts of an alginate with a desired high molecular weight.

In a sixth aspect of the present invention the pure mutant strain of *P. fluorescens* capable of producing large amounts of alginate, comprises an alginate biosynthetic operon regulated by an inducible promoter different from the naturally occurring promoter, and optionally one or more effector genes. The inducible promoter is preferably a Pm promoter, and the effector gene is xylS. According to one preferred embodiment the said mutant strain is Pf201MC.

A seventh aspect of the invention provides a method of producing the novel mutant strain of *P. fluorescens* of the invention, wherein:
(a) a wild-type strain of *P. fluorescens* is contacted with a mutagenic agent, and
(b) the treated bacteria of step (a) are grown in the presence of one or more antibiotics, and
(c) antibiotic resistant mucoid mutants are isolated by selection, and
(d) the alginate production properties of the isolated mucoid mutants of step (c) are determined.

The mutagenic agent of step (a) in the method is preferably nitrosoguanidine, and the antibiotics applied in step (b) is a β-lactam and/or aminoglycoside antibiotic, preferably the antibiotic is carbenicillin. The antibiotic may be present in the range of 800-1000 μg/ml medium, and more preferably in amounts of 900 μg/ml medium.

In still another aspect the present invention provides a method of producing a mutant strain of *P. fluorescens* capable of producing large amounts of alginate where the alginate biosynthetic operon is regulated by an inducible promoter different from the naturally occurring promoter, and optionally one or more effector genes, wherein:
(i) the alginate biosynthetic operon promoter of a wild type strain of *P. fluorescens* is exchanged by an inducible promoter by homologous recombination, and
(ii) optional effector genes are introduced into the bacterium of (i) by homologous recombination, transposon mutagenesis or by means of a plasmid, and
(iii) mutants are grown and then isolated by selection, and
(iv) the alginate production properties of the isolated mutants of (iii) are determined.

In one embodiment of the method according to the invention the inducible promoter is Pm from *P. putida* Tol-plasmid, or a mutated Pm promoter as for instance exemplified in example 9.

In still other aspects the invention comprises a method of producing a mutant strain of *P. fluorescens* of claim 8, wherein;
a) the wild type algG-gene, encoding the C-5 epimerase is cloned in a plasmid or minitransposon and mutagenized by chemical mutagenesis or by PCR,
b) a derivative of an alginate-producing strain of *P. fluorescens*, which lacks the algG gene (ΔalgG-strain), is constructed, and
c) the library of mutagenized algG of step (a) is transferred to the ΔalgG-strain of *P. fluorescens*, and the plasmid or transposon-containing strains were identified and assayed for alginate-production and epimerase-activity, and
d) the plasmid or transposon-containing strains containing a mutant algG encoding an epimerase that provides alginate with a guluronic acid residue content between 0 and 30% are identified by the assay in step (c), and
e) the mutant algG gene is cloned into a gene-replacement vector, and
f) the gene-replacement vector of step (e) is then transferred to an alginate-producing strain of *P. fluorescens* in order to replace its algG gene with the mutated algG gene, and making it capable of expressing the mutant gene.

Another aspect of the invention concerns a further method of producing a mutant strain of *P. fluorescens* of claim 8, wherein;
a) one or more amino acids, which is identified by mutagenesis and subsequent screening to be important for epimerization, is exchanged, at the gene-level, by site-specific mutagenesis to amino acids different from the ones occurring both in the mutant and the wild-type AlgG-protein, and
b) the mutant gene is cloned into a gene-replacement vector and this vector is transferred to an alginate-producing strain of *P. fluorescens* where it replaces the wild-type algG gene and is capable of being expressed.

In other aspects the invention provides use of biologically pure bacterial culture of at least one mutant strain of *P. fluorescens* as described herein for the production of alginate, and use of the alginate produced in the preparation of a food or industrial product such as a pharmaceutical, cosmetic, animal feed or nutrient product, or as an intermediate product for in vitro C-5-epimerization.

The mutant strains; Pf201, Pf2012, Pf2013, Pf20118, Pf20137, Pf20118algFΔ, Pf20118algIJΔ., Pf20118AlgLH203R, and Pf201MC of the invention have been deposited in The National Collections of Industrial Food and Marine Bacteria Ltd. (NCIMB) (Ferguson Building, Craibstone Estate, Bucksburn, Aberdeen. AB21 9YA, Scotland) the 16$^{th}$ of Jul., 2002 under the following accession numbers; 41137, 41138, 41139, 41140, 41141, 41142, 41143, 41144 and 41145 respectively. The depositions were made in accordance with the Budapest Treaty.

Definitions

The novel mutant strains and variants thereof of the present invention, produce alginate in large amounts, with "large amounts" as used herein, are meant at least 10 g alginate per liter. Amounts of 10 g alginate per liter medium are preferably achieved from 40-55 g carbon source per liter medium, more preferred from 50-55 g carbon source per liter medium or most preferred from 40 g carbon source per liter medium. The alginate yields may reach 35 g alginate per liter, but amounts of about 20% to 50% by weight of the carbon-source used, is more frequently achieved.

Suitable "carbon sources" can be selected from, but are not limited to monosaccharides, disaccharides, oligosaccharides, polysaccharides, alcohols, organic acids, and are for instance fructose, glucose, galactose, sucrose, lactose, glycerol, starch, whey, molasses, sugar sirups or lactic acid (lactate), but also other C-sources as set forth in standard textbooks, such as Bergeys Manual of Systematic Bacteriology, editors Noel R. Krieg and John G. Holt, 1984, Baltimore, USA might be equally used. It should be comprehended that the use of carbon-sources, which must not be transformed to their corresponding triose phosphates, through the Entner-Doudoroff pathway before they can be utilized for alginate production by the mutant bacteria, normally will generate the highest yields, Banerjee et al., J. Bacteriol., 1983, p. 238-245. Preferably production of more than 10 g alginate/l medium by the mutant strains of P. fluorescens of the invention, is obtained if 40 g fructose, or glycerol per liter medium is used as a carbon source. The large-scale alginate production can be carried out in any suitable manner known to a person skilled in the art, but takes preferably place in a fermentor. The fermentation is batch, fed-batch or continuous, possibly with feeding of carbon-sources and other appropriate components. The fermentation is carried out at a temperature within the interval 5-35° C. Temperatures in the lower area of this interval might be selected in certain cases, but preferably the fermentation is carried out at a temperature from 20° C. to 30° C.

Selection of media, oxygenation, pH, time of fermentation, stirring, and other possible conditions of the fermentations is deemed to be within the general knowledge of the field, and it must be understood that a vast number of combinations of two or more conditions may lead to the same high amount of alginate yield, and that the present invention is not limited to a specific combination of such conditions.

The mutant strains and the variants thereof, according to the present invention, are "stable", that is, they do not revert to strains, which do not produce alginate, when they are grown over 60 generations. The mutants were grown in PIA-medium in shake flasks under standard culturing conditions as set forth in Materials and Methods, except that the medium was replaced with fresh PIA-medium every 24 hours (successive cultivations).

The "mutant strain" used herein comprises mutant strains of P. fluorescens Pf201, as well as variant mutant strains, which all produce alginate in large amounts. In preferred embodiments, "mutant strain" refers to mutant strains of P. fluorescens Pf201 which all produce alginate in large amounts. The variants might be a result of further mutagenesis of the Pf201 mutant strain and/or further genetic engineering, or a result of genetic engineering or mutagenesis of a wild type P. fluorescens strain. The variants will produce large amounts of alginates of certain defined structures. Also variants containing any combination of the herein defined mutations are considered covered by this expression.

The alginate produced according to the invention will have a "desired molecular weight". Preferably alginate with molecular weight (Mw.) in the range from 50,000 to 3,000,000 Dalton, more preferable within 200,000 to 2,000,000 Dalton, and most preferably above 300,000 Dalton, is produced.

With the expression "biologically active alginate" used herein, is meant an alginate having an impact on a biological system, i.e. certain bioactive alginate molecular structures are known to induce biological responses in certain cellular systems. Such biological alginates have a lower content of guluronic acid (guluronate) residues, from 0 to 30% of the total uronic acid content, and preferably the guluronic acid residue content is between 1% and 15%, and more preferably within 1% and 10%.

GENERAL DESCRIPTION OF MATERIALS AND METHODS

Starting Materials and Culture Media Used for Growth of Bacteria

The bacterial strains, phages and plasmids used in the present invention are listed in Table 1 below. E. coli and P. fluorescens strains were routinely grown in LB medium (10 g/l tryptone, 5 g/l yeast extract, and 5 g/l NaCl) or on a LA-medium, which is LB-medium containing 15 g/l agar, at 37° C. and 30° C., respectively. Pseudomonas Isolation agar (PIA, Difco) was also used for propagation of P. fluorescens. E. coli used for λ phage propagation was grown in LB-medium supplemented with maltose (0.2%) and MgSO$_4$ (10 mM). Antibiotics, when used in routine growth experiments, were present at the following concentrations: Ampicillin 100-200 μg/ml, kanamycin 40 μg/ml, tetracycline 12.5 μg/ml (E. coli) and 30 μg/ml (P. fluorescens).

Production of P. fluorescens Alginate; Culture Media and Growth Conditions

Culture Media:

Production of alginate in shake flask experiments was performed in PIA-medium containing bacteriological peptone (20 g/l), MgCl$_2$ (1.4 g/l), NaCl (5 g/l), K$_2$SO$_4$ (10 g/l) and 87% glycerol (20 ml/l) or in PIA-medium with reduced salt (PIA-medium without K$_2$SO$_4$). The proteases (Alkalase 2.4 l (0.15 ml/l) and Neutrase 0.5 l (0.15 ml/l)) were added to reduce extracellular alginate lyase activity, unless otherwise stated. Alkalase and Neutrase were purchased from Novo Nordisk.

Production of alginate in fermentor was performed in PM5-medium containing: fructose (40 g/l), yeast extract (12 g/l), $(NH_4)_2SO_4$ (0.6 g/l), $Na_2HPO_4 \times 2H_2O$ (2 g/l), NaCl (11.7 g/l), $MgSO_4 \times 7H_2O$ (0.3 g/l) and clerol FBA622 (antifoam) (0.5 g/l). The proteases (Alkalase 2.4 l (0.25 ml/l) and Neutrase 0.5 l (0.25 ml/l) were added to reduce extracellular alginate lyase activity.

Preparation of Standard Inoculum (Frozen Culture with Glycerol as Cryoprotectant)

A colony from agar plate (incubated at 30° C. for 2-3 days, PIA-medium) is transferred to a shake flask (500 ml, baffled) with 100 ml LB-medium. The shake flask is incubated at 30° C. for 16-20 hours in an orbital shaker (200 rpm, amplitude 2.5 cm). For preservation sterile glycerol is added to the broth to a concentration of 15%. The mixture is transferred to sterile cryo vials (Nunc) and stored at −80° C.

Preparation of Inoculum for Production Experiments in Shake Flasks and Fermentor 1 ml standard inoculum is transferred to a shake flask (500 ml, baffled) with 100 ml LB-medium. The shake flask is incubated at 30° C. for 16-20 hours in an orbital shaker (200 rpm, amplitude 2.5 cm).

Alginate Production in Shake Flask 1-2 vol-% inoculum (see above) is transferred to a shake flask (500 ml, baffled) with 100 ml PIA-medium or PIA-medium with reduced salt. The shake flask is incubated at 25° C. for 48 hours in an orbital shaker (200 rpm, amplitude 2.5 cm).

Alginate Production in Fermentor 2-3 vol-% inoculum from shake flask is transferred to a 3-liter fermentor (Applicon), with 1.4 liter PM5-medium. The fermentations are performed at 25° C. pH from start is adjusted to 7.0-7.2 pH is controlled at 7.0 with NaOH (2 M) and the pH-control is activated when the pH reaches this value. The airflow through the culture medium is 0.25 liter/liter medium (vvm) for the first 8-10 hours, thereafter it is increased in steps up to 0.9-1.0 vvm. The dissolved oxygen is controlled at 20% of saturation by automatic control of the stirrer speed.

Applied Standard Techniques

Plasmid isolation, enzymatic manipulations of DNA and gel electrophoresis were performed by the methods of Sambrook and Russell, 2000, Molecular Cloning: A Laboratory Manual (Third Edition). Cold Spring Harbor Laboratory Press. Qiaquick Gel Extraction Kit and Qiaquick PCR purification kit (Qiagen) was used for DNA-purifications from agarose gels and enzymatic reactions, respectively. Transformation of E. coli was performed as described by Chung et al., 1989, Proc Natl Acad Sci USA, 86, p. 2172-2175 or by use of heat-shock-competent rubidium chloride cells. PCR for cloning and allele identification was performed using the Expand High Fidelity PCR-system (Boehringer Mannheim). As templates were used either plasmid DNA or 1 µl of an over-night P. fluorescens culture. In the first denaturation step the reaction mixtures were heated to 96° C. for three minutes to ensure both cell lysis and full denaturation of the DNA. Site-specific mutagenesis was performed using QuickChange Site-Directed Mutagenesis Kit (Stratagene). Primers given in Table 2 were purchased from Medprobe or from MWG-Biotech AG. Nucleotides in the primers, which are different from those of the wild-type sequence are written in bold, and restriction-enzyme sites are underlined. DNA sequencing was performed using a Big-Dye kit (Applied Biosystems).

Construction of Suicide Vectors for Use in P. fluorescens

Figure 1:
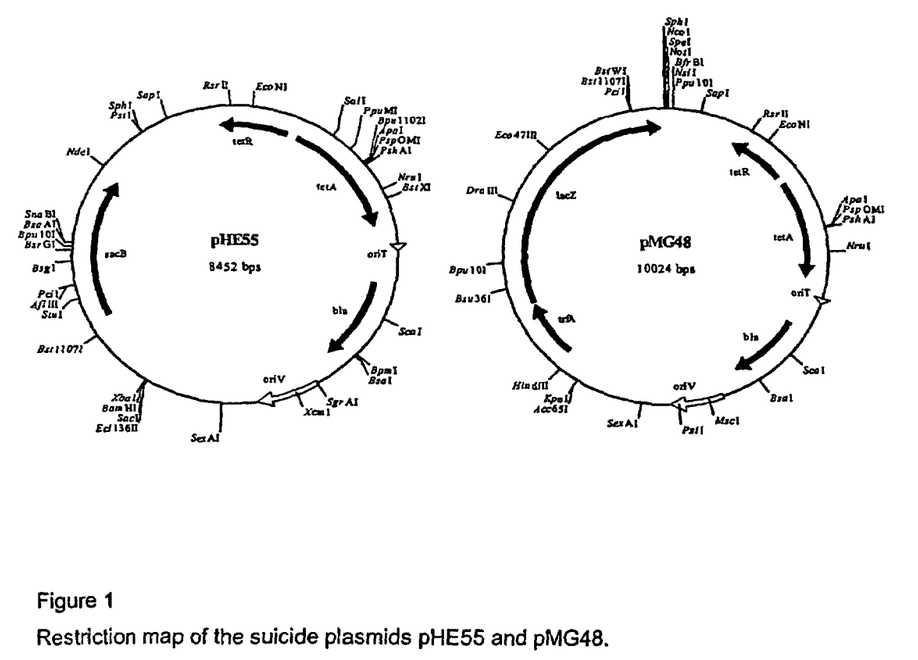
FIG. 1: Restriction endonuclease maps of the suicide vectors pHE55 and pMG48, confer Table 1. Only unique restriction enzyme sites shown.

In order to achieve homologous recombination in P. fluorescens two different suicide vectors, pHE55 and pMG48, were constructed, confer FIG. 1. The construction of pHE55 is described in Table 1. It is an RK2-based vector lacking the gene encoding TrfA, which is necessary for replication of the plasmid. It further confers resistance to ampicillin and tetracycline, which can be used for selecting integrants. Expression of sacB encoding levan sucrase from Bacillus subtilis has been shown to be lethal for many gram-negative bacteria when grown on 5% sucrose (Gay et al., 1985, J. Bacteriol., 164, p. 918-921). In strain NCIMB 10525 of P. fluorescens, however, growing non-mucoid and tetracycline resistant transconjugants on sucrose resulted in glassy colonies, as if the strain uses the sucrose to produce a polymer. SacB and sucrose selection could then not be used for this strain to positively select double cross-overs. pHE55 was used as a suicide vector in some experiments, where alginate production could be used as a marker.

The plasmid pMG48 was constructed as an alternative recombination vector. The sacB-gene of pHE55 was replaced by a gene encoding a TrfA-LacZ-fusion protein, as described in Table 1. This protein shows β-galactosidase activity, but the essential parts of TrfA is missing. Using plates containing XGal (5-Bromo-4-chloro-3-indolyl β-D-galactopyranoside), 60 µl of a 20 mg/ml stock solution was added to each agar plate used for screening. The β-galactosidase activity allow for blue/white screening both for integrants (blue colonies) and later for the second recombination event (white colonies).

Homologous Recombination

The DNA sequence containing the mutation of interest, either a point-mutation, insertion or deletion together with flanking DNA of at least 0.5 kb on each side was cloned into a suicide vector, either pHE55 or pMG48. E. coli S17.1 transformed with the plasmid of interest and the P. fluorescens strain to be mutated were incubated in LB-medium overnight. They were then incubated in fresh LB-medium, 1% inoculum was used. E. coli was grown for two hours, P. fluorescens for four hours prior to conjugation. One ml of each culture were then mixed and centrifuged for 15 min. at 3000 rpm. Most of the supernatant was removed, and the cells were resuspended in the remaining liquid. The droplet containing the cells was transferred to LA-medium, and incubated at 30° C. over-night. The cells were removed by a sterile spatula, resuspended in LB-medium, and dilutions were plated on Pseudomonas Isolation agar (PIA, Difco) with appropriate antibiotics and X-Gal when the vector allowed for blue/white selection. A non-mucoid transconjugant colony of each mannuronan-producing strain was incubated in 2-6 sequential liquid over-night cultures in the absence of tetracycline to allow loss of the integrated plasmid. Exponentially growing cultures were diluted $10^4$-$10^9$ fold and plated on the appropriate medium to screen for the different strains.

Measurement of G-Content and Degree of O-acetylation of the Alginate by NMR-spectroscopy.

Samples from fermentations were diluted in 0.2 M NaCl and centrifuged to remove the bacterial cells. For preparation of samples for determination of degree of acetylation, alginate was precipitated from the cell free supernatant by addition of one volume isopropanol (4° C.), and thereafter collected by centrifugation. The precipitated alginate was then washed twice with 70% ethanol, once in 96% ethanol, and redissolved in distilled water before further treatment. For preparation of samples for determination of G-content the alginate in the cell free supernatant was deacetylated by mild alkaline treatment as described in Ertesvåg and Skjåk-Bræk, 1999, in Methods in biotechnology 10, Carbohydrate Biotechnology Protocols. Bucke, pp 71-78. Humana Press Inc. Deacetylated alginate was isolated from the cell free supernatant by acid precipitation by adding HCl to pH 2. The precipitated alginate was collected by centrifugation, redissolved in distilled water and neutralized by alkali. To reduce the viscosity of the polymer for NMR analysis the samples were degraded by mild acid hydrolysis to a final average degree of polymerisation (DPn) of about 35, that is 35 residues in the polymer chain, neutralized and freeze dried, Ertesvåg and Skjåk-Bræk, 1999, supra. NMR-spectra were obtained using a Bruker 300-MHz Spectrometer. The spectra were integrated, and the fractions of guluronate residues ($F_G$), mannuronate block residues ($F_{MM}$) and alternating block residues ($F_{MG=GM}$) and degree of acetylation were calculated as described in Grasdalen, 1983, Carbohydr. Res., 118, p. 255-260 and Skjåk-Bræk, Grasdalen and Larsen, 1986, Carbohydr. Res., 154, p. 239-250.

Measurement of the Intrinsic Viscosity of the Alginate and Direct Measurement of Alginate Content in Fermentation Samples.

The alginate produced was isolated, deacetylated, acid precipitated, redissolved and neutralized as described above. The neutralized alginate solution was added isopropanol to precipitate the alginate a second time. The precipitated alginate was washed twice with ethanol (first 70% and then 96% ethanol), redissolved in distilled water and dialyzed against distilled water for 48 hours. After dialysis the sample was freeze dried and weighed. The intrinsic viscosity of the alginates was determined on a Scott-Geräte apparatus with automatic dilution, using an Ubbelodhe capillary ($\Phi$=0.53 mm) at 20° C. and an added salt concentration of 0.1 M NaCl. The principle of the method is as described in Haug and Smidsrød, 1962, Acta. Chem. Scand., 16, p 1569-1578.

Enzymatic Determination of Alginate Content in Fermentation Samples.

Alginate content was measured using the M-specific lyase from abalone and G-lyase from *Klebsiella aerogenes* as described by Østgaard, 1992, 19, Carbohydr. Polymers, p. 51-59.

Samples from fermentations were diluted (2-20 times) in 0.2 M NaCl, centrifuged to remove bacterial cells, and deacetylated, as described above. The deacetylated samples were then diluted in buffer (Tris-HCl (50 mM), NaCl (0.25M), pH 7.5) to a final concentration of 0.005-0.05% alginate. LF 10/60 (FMC Biopolymer AS) or mannuronan, produced and measured as described herein, were used as alginate standards in the assay. For the assay one volume of sample, or standard and 0.06 volumes of alginate lyase solution (about 1 u/ml) are added to two volumes of buffer (Tris-HCl (50 mM), NaCl (0.25M), pH 7.5) and incubated for 3 hours at 25° C. The absorbance at 230 nm is recorded before and after the incubation. The differences in the A230 nm values before and after the incubation are used for calculation of the alginate content in the sample. The results, using this assay, correlate very well with the direct measurement of alginate content described above.

Determination of Lyase Activity

Bacterial cells from fermentations were collected by centrifugation, resuspended in buffer (Tris-HCl (50 mM), NaCl (0.25M), pH 7.5) to an optical density of 3-10 at 660 nm and sonicated. The extracts after sonication were investigated for lyase activity. M-specific lyase from abalone (described by Østgaard, 1992, 19, Carbohydr. Polymers, p. 51-59) was used as standard. The lyase activities in samples were determined by measuring the degradation rate of mannuronan using a Scott-Geräte Ubbelodhe (instrument nr. 53620/II). Mannuronan (1 mg/ml) was dissolved in buffer (Tris-HCl (12.5 mM), NaCl (62.5 mM), pH 7.5). 4 ml of mannuronan substrate solution and 0.4 ml of diluted standard solution, or sample were added to the Ubbelodhe capillary. The time for the solution to pass the capillary of the Ubbelodhe was measured every 2 minute over a time period of one hour. The analysis was performed at 25° C. Based on the data from the analyses, the degradation rate of mannuronan was calculated and correlated to the lyase activity in the sample. A standard curve was obtained using the abalone M-lyase as a standard (0.005-0.05 u/ml). 1 unit of lyase activity is defined as described by Ertesvåg et al., J. Bacteriol. (1998),180, p. 3779-3784.

TABLE 1

Bacterial strains, plasmids and phages used

| Strains | Description | Reference |
|---|---|---|
| *E. coli* S17.1 | recA1 supE44 endA1 hsdR17 gyrA96 relA1 thiΔ (lac-proAB), contains the necessary genes for replication and transfer of RK2. | Simon et al, 1983, Biotechnol. 1, p. 784-791. |
| *E. coli* S17.1λ-pir | λ-pir, recA1 supE44 endA1 hsdR17 gyrA96 relA1 thiΔ (lac-proAB), contains the necessary genes for replication and transfer of RK2 and replication of pCB111 | de Lorenzo et al, 1993, J. Bacteriol. 175, p. 6902-6907. |
| *E. coli* SURE | e14-(McrA-) D(mcrCB-hsdSMR-mrr)171 endA1 supE44 thi-1 gyrA96 relA1 lac recB recJ sbcC umuC::Tn5 (Kanr) uvrC [F' proAB laclqZD(M15 Tn10 (Tetr)] | Stratagene |
| *E. coli* XL1-Blue MRA | Δ(mcrA) 183 Δ(mcrCB-hsdSMR-mrr) 173 endA1 supE44 thi-1 gyrA96 relA1 lac | Stratagene |
| *E. coli* XL1-Blue MRA(P2) | XL1-Blue MRA (P2 lysogen) | Stratagene |
| *P. fluorescens* NCIMB10525 | Non mucoid *P. fluorescens* wild type | NCIMB |
| Pf201 | algG+, mucoid *P. fluorescens* | This work |
| Pf2012 | mannuronan-producing mutant, algG⁻D361N | This work |
| Pf2013 | mannuronan-producing mutant, algG G430D | This work |
| Pf20118 | mannuronan-producing mutant, algG R408L | This work |
| Pf20137 | mannuronan-producing mutant, algG S337F | This work |
| Pf20118algFΔ | algF in-frame deletion mutant of Pf20118. | This work |

TABLE 1-continued

Bacterial strains, plasmids and phages used

| Strains | Description | Reference |
|---|---|---|
| Pf20118algIJΔ | algIF in-frame deletion mutant of Pf20118. | This work |
| Pf20118algLΔ | algL in-frame deletion mutant of Pf20118 | This work |
| Pf20118algLH203R | Pf20118-derivate encoding the AlgLH203R mutant protein | This work |
| Pf201ΔalgG | algG in-frame deletion mutant | This work |
| Pf20118::TnKB10 | Derivative of Pf20118 with transposon from pKB10. | This work |
| Pf201ΔalgG::TnKB10 | Derivative of Pf201ΔalgG with transposon from pKB10. | This work |
| Pf201MC | Derivative of Pf201 in which the alginate biosynthesis is controlled by the inducible promoter Pm. | This work |
| Phages | | |
| λDashII | λ cloning vector | Stratagene |
| Pfλ1 | λ DashII in which an 15 kb insert of SauAI-partially digested genomic DNA from *P. fluorescens* NCIMB10525 containing alg'EGXLIJFA has been inserted. | This work |
| Plasmid | | |
| pCVD442 | Ori R6K, Ap$^r$ | Donnenberg and Kaper, 1991, 59, p. 4310-4317. |
| pJB3Tc20 | RK2-based vector, Ap$^r$, Tc$^r$ | Blatny et al., 1997, Appl. Environ. Microbiol., 63, p. 370-379. |
| PJB3Tc20trfA | Derivative of pJB3Tc20 from which a 1.0 kb BsaAI-NdeI-DNA-fragment encoding TrfA was deleted. | This work |
| pHE55 | Derivative of pJB3Tc20trfA in which a 2.6 kb PstI-XbaI-DNA-fragment from pCVD442 encoding SacB from *Bacillus subtilis* was inserted. | This work |
| pJB1002 | RK2-based vector encoding a TrfA-LacZ-fusion protein | Karunakaran et al., 1998, J. Bacteriol, 180, p. 3793-3798. |
| pGEM5 | ColE1. Ap$^R$. | Promega |
| pMG47 | Derivative of pHE55 in which a 4.1 kb NheI-PstI-DNA-fragment from pJB1002 encoding a TrfA-LacZ-fusion protein replaced a 2.6 kb XbaI-PstI DNA-fragment encoding SacB: | This work |
| pMG48 | Derivative pMG47 in which a 0.36 kb SphI-SapI DNA-fragment containing the polylinker of pGEM5 has been inserted. | This work |
| pBBg10 | 9.9 kb BglII-BamHI insert from the *Pseudomonas aeuginosa* alginate biosynthetic operon containing alg'KEGXLIJF. Ap$^r$. | Gift from A. Chakrabarty. |
| pGEM11 | ColE1. Ap$^R$. | Promega |
| pMG24 | pGEM11 containing a 1 kb SalI-DNA-fragment from Pfλ1 encoding part of algE. | This work |
| pMG25 | pGEM11 containing a 4.2 kb SalI DNA-fragment from Pfλ1 encoding sequences downstream of the alginate operon. | This work |
| pMG26 | pGEM11 containing a 4.6 kb SalI-DNA-fragment from Pfλ1 encoding algGXLI'. | This work |
| pMG27 | pGEM11 containing a 4.8 kb SalI-DNA-fragment from Pfλ1 encoding alg'IJFA. | This work |
| pLitmus28 | ColE1. Ap$^R$. | New England Biolabs |
| pMG23 | pLitmus28 in which a 1.8 kb PCR amplified BglII-Pst1 DNA-fragment containing algG and 135 bp of algX was inserted. The primers PfalgG3r and PfalgG4f were used. | This work |
| pMG31 | Derivative of pHE55 in which an 1.8 kb BglII-XbaI-DNA-fragment encoding AlgG from pMG23 was inserted. | This work |
| pMG49 | pMG27-derivate from which a 1.4 kb NruI-HpaI DNA-fragment was deleted, creating an in frame algI''J-deletion | This work |
| pMG50 | pHE55 with 3441 bp SacI-XbaI insert from pMG49 containing algIJΔ. | This work |
| pMG77 | Derivative of pMG27 where a SacII-site was introduced using the primerpair algF-SacII-1 and algF-SacII-2 (table 2). | This work |

TABLE 1-continued

Bacterial strains, plasmids and phages used

| Strains | Description | Reference |
|---|---|---|
| pMG78 | Derivative of pMG77 from which a 285 bp SacII-DNA fragment in algF was deleted. | This work |
| pMG79 | Derivative of SphI-SpeI-restricted pMG4B in which a 1.7 kb NspI-NheI-DNA fragment from pMG78 was inserted. | This work |
| pMG67 | Derivative of pMG26 in which an AgeI-site and an algLH203R was introduced using the primers AlgLH203R1 and AlgLH203R2. | This work |
| pMG70 | Derivative of pMG48 into which a 2.5 kb PstI-NotI-DNA-fragement from pMG67 was inserted into the NsiI and NotI-sites of the vector | This work |
| pJB658 celB | Expression vector containing the Pm-promoter and xylS. Ap$^r$. | Blatny et al., 1997, Plasmid, 38, p. 35-51. |
| pHE138 | Derivative of pJB658celB in which a 0.8 kb NdeI-NsiI-digested PCR-fragment encoding the N-terminal part of AlgD was inserted into the NdeI and PstI-sites replacing celB. | This work |
| pHE139 | Derivative of pMG48 in which a 0.7 kb BspLUIII-SpeI-digested PCR-fragment encoding the C-terminal part of the ORF upstream of the alginate promoter was inserted into the NcoI and SpeI-sites. | This work |
| pHE140 | Derivative of pHE138 from which a 0.6 kb NsiI-DNA-fragment had been removed, and the protruding ends removed by T4-DNA-polymerase. | This work |
| pHE141 | A BglII-linker was inserted into NsiI-digested pHE139 which had been made blunt using T4-DNA-polymerase. | This work |
| pHE142 | A NotI-linker was inserted downstream of xylS in pHE140 partially digested with Eco57I. | This work |
| pMC1 | A 2.3 kb NotI-BamHI-DNA-fragment from pHE142 was inserted into NotI-BglII-digested pHE141. | This work |
| pMG51 | Derivative of pMG26 where a SmaI-site was introduced at nucleotide position 368 in algG using the primers algG-SmaI-1 and algG-SmaI-2. | This work |
| pMG52 | Derivative of pMG51 from which a 0.6 kb SmaI-DNA-fragment was deleted creating an in-frame deletion in algG. | This work |
| pMG53 | Derivative of NsiI-NcoI-restricted pMG48 in which a 2.1 kb Pst1-BspHI-DNA fragment from pMG52 was inserted. | This work |
| pCNB111 | oriR6K, mobRP4, pUT/mini-Tn5 xylS/Pm, Ap$^r$, Km$^r$. | Winther-Larsen et al., 2000, Metabol. Eng. 2 p 79-91 |
| pKB4 | Derivative of pMG26 from which a 3.0 kb BlpI-XhoI-DNA fragment was deleted. Ap$^r$. 4.9 kb. | This work |
| pKB10 | Derivative of pCNB111 in which a 1.7 kb NdeI-NotI restricted PCR-fragment containing algG was inserted. pKB4 was used as PCR-template, PfalgG-NdeI-2 and M13/pUC reverse as primers. | This work |
| pJT19bla | Derivative of pJB655 encoding β-lactamase controlled by the Pm-promoter | Winther-Larsen et al., 2000, Metabol. Eng. 2 p 92-103. |
| pJT19D2luc | Derivative of pJT19bla. Encodes the luc-gene as reporter gene | Winther-Larsen et al., 2000, Metabol. Eng. 2 p 92-103. |
| pIB11 | Derivative of pJT19bla containing a rrnBT1T2 terminator upstream of the Pm-promoter, and the SpeI site has been changed to a BspLU11I-site | Ingrid Bakke, unpublished |
| pHH100 | Derivative of pIB11 where the bla-gene was replaced by a luc-gene from pJT19D2luc using the enzymes NdeI and BamHI. | This work |
| pHH100-A2 | Derivative of pHH100 containing a mutant Pm-promoter giving lower uninduced activity. | This work |
| pHH100-B1 | Derivative of pHH100 containing a mutant Pm-promoter giving lower uninduced activity. | This work |
| pHH100-D6 | Derivative of pHH100 containing a mutant Pm-promoter giving lower uninduced activity. | This work |

TABLE 1-continued

Bacterial strains, plasmids and phages used

| Strains | Description | Reference |
|---|---|---|
| pHH100-D9 | Derivative of pHH100 containing a mutant Pm-promoter giving lower uninduced activity. | This work |
| pHH100-G5 | Derivative of pHH100 containing a mutant Pm-promoter giving lower uninduced activity. | This work |
| pHM2 | Broad-host-range plasmid enoding lacOPZY from E. coli | Mostafa et al. 2002. Appl. Environment. Microbiol. 68: 2619-2623 |

TABLE 2

Primers used

| Name | Sequence* |
|---|---|
| PfalgG3r | CAGGCTGCAGCACGGTTCGGC |
| PfalgG4f | AAAAAGATCTAGTCGACTCGTACATGCACC |
| PfacetylFw | CTGCTGGTGGTGATGGGCTGGG |
| PfacetylRev | AGACGCGCACGAAGCTTGAGCC |
| algF-SacII-1 | GTCAAACTCGCCGCGGATCACTAC |
| algF-SacII-2 | GTAGTGATCCGCGGCGAGTTTGAC |
| algF-1-Fw | AGCGATGACTTCAAGAACAACCCG |
| algF-2-Rev | CAATTTGGGTCAGAGCTACGAAGG |
| algLH203R1 | AACCAACAACCGGTCCTACTGGGCCGCC3' |
| algLH203R2 | GGCGGCCCAGTAGGACCGGTTGTTGGTT |
| PfalgL-BspHI-pMG26 | AAAAAAAGTC ATGAGGTTACCTATGCAGAAGTTATTG |
| algG-SmaI-1 | CACGGCATTCCCCGGGCGATCTTC |
| algG-SmaI-2 | GAAGATCGCCCGGGGAATGCCGTG |
| PfalgG-NdeI-2 | AAAAAACATATGGGAGCCTGCGCAATGAACC |
| PfalgLRev1 | AAAGATCGGCAAGAACAGAAACAGG |
| HypBspLUIII | GTTACATGTCAGCCGCAATACCTCGACC |
| HypSpe | GTTACTAGTTTATTCGGGGCGTGATCG |
| AlgDNdeI | GGTAATTCATATGCGCATCAGCATATTTG |
| AlgDNsiI | GTAATGCATGTAGTACTGGGACAGG |

*The primers are written in the 5'-3' direction. Nucleotides not found in the original sequence are shown in bold. Introduced restriction-sites are underlined.

EXAMPLES OF THE INVENTION

Example 1

Preparation of Mutant Strain Pf201

The wild type *P. fluorescens* NCIMB 10525 was purchased from The National Collections of Industrial Food and Marine Bacteria Ltd. (NCIMB). The wild type does not produce significant amounts of alginate. In order to isolate alginate over-producing mutants exponentially growing cells of *P. fluorescens* NCIMB 10525 were subjected to nitrosoguanidine (NG) mutagenesis. The strain was grown in nutrient broth (CM67, Oxoid) with 0.5% yeast extract and washed twice in 0.1 M citrate buffer (pH 5.5) before treating the cells with 25 ug/ml nitrosoguanidine (NG) in citrate buffer for 1 hour at 30° C. The mutagenized cells were washed with 0.1 M phosphate buffer pH 7.0 containing $KH_2PO_4$ (13.6 g/l) and NaOH (~2.32 g/l) and inoculated (2%) into nutrient broth with yeast extract. The cells grew overnight and were then frozen as 1 ml aliquots of NG-stock.

Figure 2:
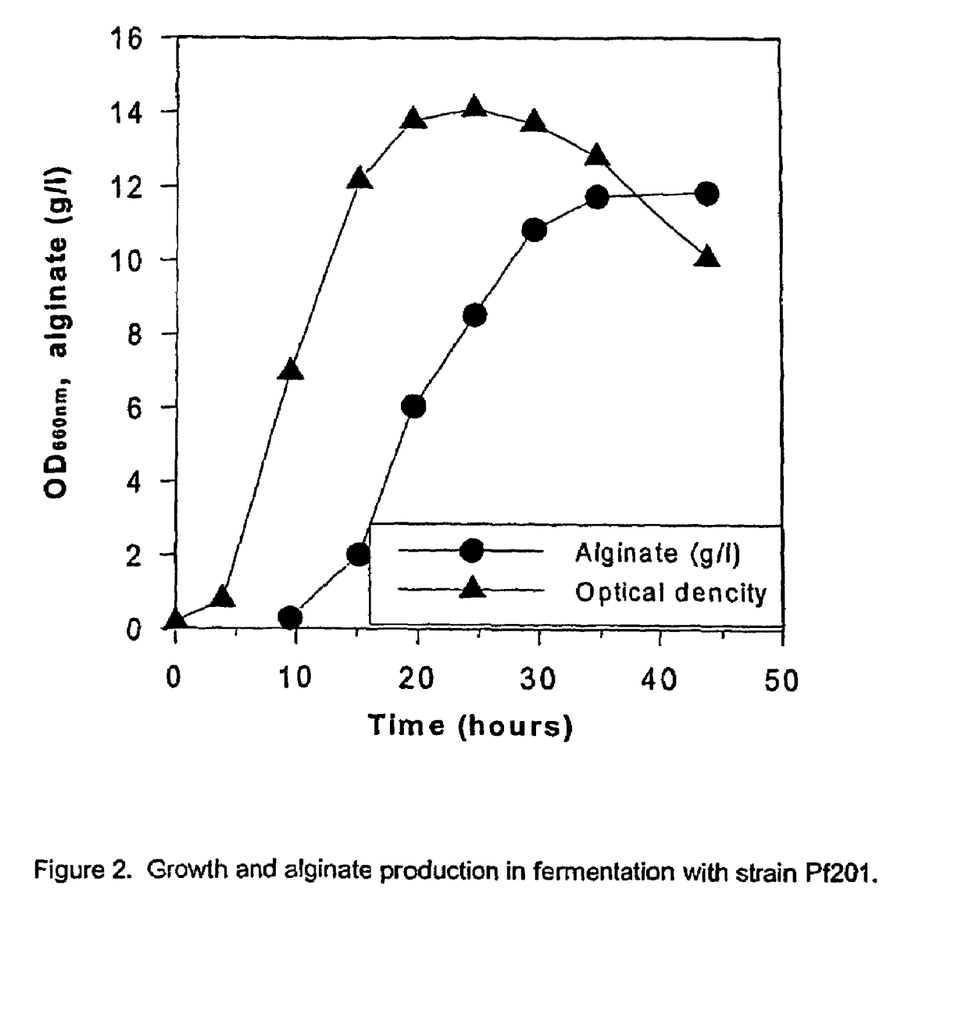
FIG. 2: Growth and alginate production in fermentations with mutant strains of P. fluorescens NCIMB 10525.
Figure 3:
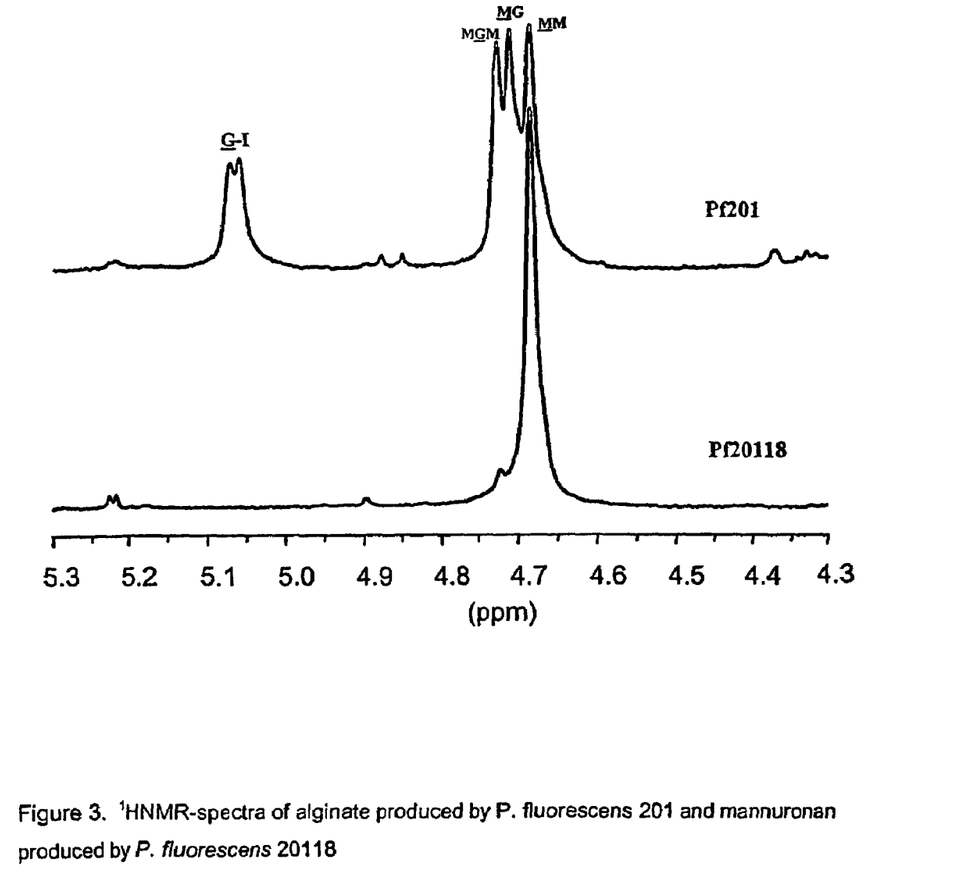
FIG. 3: $^1$H-NMR-spectra of alginate produced by P. fluorescens mutant strains Pf201 and Pf20118. The $^1$H-NMR-spectra of mannuronan from the other epimerase negative mutants (Table 3) were identical with the one for Pf20118.

Dilutions of the culture were plated on PIA-medium containing carbenicillin (900 μg/ml) and incubated at 30° C. A few mucoid mutants were observed. From the screening, which included inspection of more than $4*10^5$ colonies, the two most mucoid mutants were selected for further evaluation in fermentor studies. The better mutant, Pf201 yields in fermentation 11-13 g alginate per liter PM5-medium containing 40 g fructose as carbon source per liter, as depicted in FIG. 2. For growth conditions and medium composition, it is referred to Materials and Methods. The alginate produced by the Pf201 mutant using the PM5-medium containing fructose, and under standard growth conditions, contains about 30% G (guluronate residues) with complete absence of G-blocks as can be estimated from FIG. 3. Based on the unique alginate production properties, the Pf201 strain was selected for further strain development. The *P. fluorescens* mutant Pf201 of example 1 is deposited in NCIMB under the accession number 41137.

Example 2

Cloning and Sequencing of Parts of the Alginate Biosynthetic Operon

Figure 4:
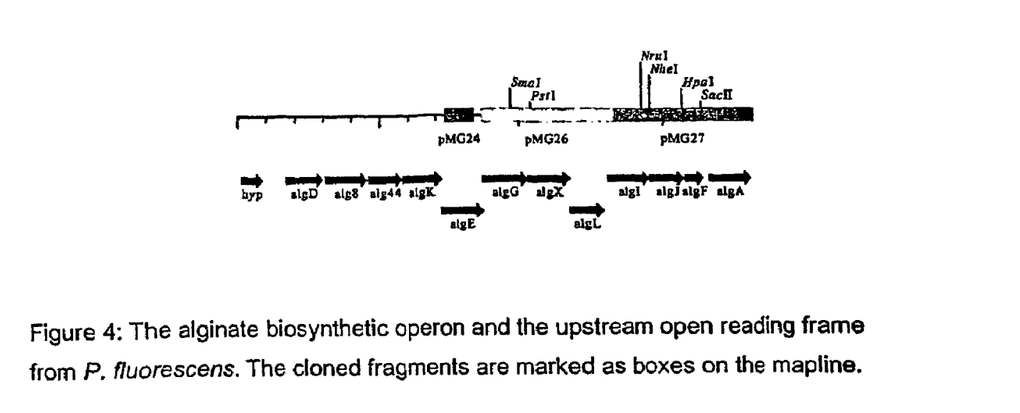
FIG. 4: The alginate biosynthetic operon and the upstream open reading frame from P. fluorescens are shown. The cloned fragments are marked as boxes on the map line. Only restriction sites used for cloning are shown. The total length is 18 kb.

A gene library of the wild-type strain NCIMB 10525 was constructed in λDASH II (lambda Dash II) (purchased from Stratagene). Chromosomal DNA was isolated as described by Ausubel et al., 1993, Current protocols in molecular biology. Greene Publishing Associates, Inc and John Wiley & Sons Inc, New York. The gene-library was then constructed by inserting partially Sau3AI-digested chromosomal DNA from NCIMB 10525 into BamHI-digested lambda Dash II and infecting *E. coli* XL1Blue MRA(P2) with the in vitro-packaged phages according to the manufacturers instructions (Stratagene BamHI/Gigapack III Gold Extract). Labeling of DNA-probe and detection of hybridizing λ-clones were done by use of DIG DNA Labeling and Detection Kit (Boehringer Mannheim) according to the manufacturers instructions. A 3.8 MfeI-NcoI DNA-fragment from pBBg10 containing algG flanked by parts of algE and algX from *P. aeruginosa* was labeled and used to screen the *P. fluorescens* library. One hybridizing phage, designated Pfλ1, was detected using this system and λ DNA was isolated using Lambda Midi Kit (QIAGEN). The insert was subcloned as SalI-digested DNA-fragments into pGEM11 resulting in the four subclones pMG24-27. Sequencing of the ends of the subclones and comparison with the alginate biosynthetic operon of *P. aeruginosa* revealed that Pfλ1 contains the downstream part of the alginate biosynthetic operon from the 3' part of algE (FIG. 4).

pMG26 and pMG27 were sequenced by Quiagen Sequencing & Genomics to obtain the full sequence of algGXLIJFA. This gene organization seems to be similar to previously reported alginate biosynthetic clusters in; May and Chakrabarty, 1994, Trends Microbiol., 2, p. 151-157, Rehm et al., 1996, J. Bacteriol., 178, p. 5884-5889, Penaloza-Vazquez et al., 1997, J Bacteriol., 179, p. 4464-4472, Vazquez et al., 1999, Gene, 232, p. 217-222. The sequence has been submitted to GenBank and given the accession number AF527790.

Example 3

Preparation of Epimerase Negative Variant Strains

The mutant strain Pf201 of Example 1 was subjected to further mutagenesis using nitrosoguanidine using a modification of the method described in Example 1. Exponentially growing cells of *P. fluorescens* NCIMB 10525 were subjected to nitrosoguanidine (NG) mutagenesis: The bacterial cells were washed twice with equal volume of Tris/maleic acid (TM) buffer pH 6.0 containing $NH_4SO_4$ (1.0 g/l), $CaCl_2*2H_2O$ (4.4 mg/l), $KNO_3$ (6.1 mg/l), maleic acid (5.8 g/l), Tris (hydroxy methyl)-amino methane (6.05 g/l), $FeSO_4*7H_2O$ (0.25 mg/l) and $MgSO_4*7H_2O$ (0.1 g/l). Cells were re suspended in 80% of original culture volume of TM-buffer and exposed to NG (50 μg/ml) for 1 hour at 30° C. The mutagenized cells were washed with 0.1 M phosphate buffer pH 7.0 containing $KH_2PO_4$ (13.6 g/l) and NaOH (~2.32 g/l) and inoculated (2% inoculum) into LB-medium and incubated over-night. The death rate of the mutagenesis procedure was calculated to approximately 90% using a non-mutagenized aliquot of the culture as control. After mutagenesis the culture was grown in LB-medium over-night, and dilutions of the cells plated on LA-medium containing G-lyase from *Klebsiella aerogenes* (about 0.1 u/dish), as described by Chitnis. et al, 1990, J. Bacteriol., 172, p. 2894-2900. This G-lyase cleaves only the G-M (guluronate-mannuronate residue) and the G-G (guluronate-guluronate residue) bonds in alginate, Haugen et al, 1990, Carbohydr. Res., 198, p. 101-109.

Mucoid mutants appeared at a frequency of about 1 in 7500 on such selective plates. One mucoid mutant was isolated and designated Pf20118. Pf20118 was grown in a fermentor under standard growth conditions using PM5 medium, confer Materials and Methods. The polymer produced was analyzed by $^1$H-NMR spectroscopy. The results of this analysis showed that the mutant produced pure mannuronan, confer FIG. 3. Several fermentations were performed with Pf20118 using standard growth conditions and the PM5-medium. Volumetric yields were in the range of 14-16 g mannuronan per liter from 40 g fructose per liter medium, in approximately 35 hours fermentations. The *P. fluorescens* mutant Pf20118 derived from Pf201 was subject to more than 70 different experiments in fermentor, none of which have indicated instability in the mannuronan producing properties. Both Pf201 and Pf20118 have been grown for 60 generations without the appearance of non-mucoid colonies. Although it seemed probable that Pf20118 had a defect in the mannuronan C-5-epimerase gene algG, it could not be excluded that the mutations affected other proteins, which somehow could be necessary for epimerization. A preliminary localization of the mutations responsible for the mannuronan producing phenotype was performed by gene-replacement of the algG allele in each of the mutants by wild-type algG. A gene-replacement vector, pMG31, encoding wild-type algG and the first 135 bp of the downstream algX was constructed as described in Table 1. The plasmid was conjugated into the Pf20118 as described in Materials and Methods using PIA containing tetracycline as selective medium. Non-mucoid colonies appeared due to the disruption of the alginate biosynthetic operon as pMG31 recombined into algG. A non-mucoid transconjugant colony was incubated in 2-6 sequential liquid over-night cultures in the absence of tetracycline to allow loss of the integrated plasmid. Exponentially growing cultures were diluted $10^4$-$10^9$ fold and plated on PIA agar plates to screen for mucoid revertants. Mucoid colonies were then re-streaked on L-agar containing G-lyase to test if they produced epimerized alginate. Such non-mucoid revertants were found, confirming that the mutation had to be in the DNA-fragment corresponding to the algGX' fragment of pMG31. The algG-gene was amplified by PCR using the primers PfalgG3r and PfalgG4f, sequenced and the mutation identified, confer Table 3.

Three other epimerase negative mutant derivative strains were prepared according to the procedure set forth above, and designated Pf2012, Pf2013, and Pf20137 respectively. They all have an identified mutation in their algG gene resulting in a different amino acid in their AlgG gene product, as set forth in Table 3 below, and this amino acid change is sufficient to inactivate the protein. The mutants yielded approximately the same levels of pure mannuronan as Pf20118, when grown under the same conditions. The epimerization defect of the mutants could be reverted by recombination with the wild type gene in pMG31.

TABLE 3

Mutations in algG in mannuronan-producing mutants

| Mutant | Mutation in algG | Amino acid substitution in gene product |
|---|---|---|
| Pf2012 | G(1081) → A(1081) | Asp(361) → Asn(361) |
| Pf2013 | G(1289) → A(1289) | Gly(430) → Asp(430) |
| Pf20118 | C(1222) → T(1222) | Arg(408) → Leu(408) |
| Pf20137 | C(−3) → T(−3) | — |
|  | C(1010) → T(1010) | Ser(337) → Phe(337) |

The mutant strains of table 3 were deposited in NCIMB under the accession numbers; Pf2012 has the NCIMB no. 41138, Pf2013 has the NCIMB no. 41139, Pf20118 has the NCIMB no. 41140 and Pf20137 has the NCIMB no. 41141.

Example 4

Preparation of Acetylase Negative and Modified Variant Strains, Pf20118algFΔ and Pf20118algIJΔ.

A Pf20118 algF deletion mutant was first made, by constructing a mutant DNA-fragment containing flanking sequences of an in-frame deletion of parts of algF, and then ligate the fragment into the suicide vector pMG48, as described in Table 1. The resulting plasmid, designated pMG79, was transferred to *P. fluorescens* strain Pf20118 by conjugation as described in Materials and Methods, and the transconjugants were selected as blue colonies on PIA-plates containing XGaI and tetracycline. Double recombinants were selected as white and mucoid colonies on PIA-plates containing XGaI. These candidates were further tested for sensitivity to tetracycline. Twenty-four white, tetracycline sensitive candidates were tested by PCR using the primer-pair algF-1-fw and algF-2-Rev as given in Table 2, and the products were analyzed by gel electrophoresis. PCR-products from twenty-two of the candidates had the length expected for the wild-type algF-allele (1.0 kb). However, the two others had the expected length for the mutant ΔalgF-allele (0.7 kb). One of these was designated Pf20118algFΔ.

A deletion mutant of algIJ was created by first creating a derivative (pMG49) of pMG27 from which a 1.4 kb NruI-HpaI DNA-fragment containing the 261 3' nucleotides of algI and the 5' 1140 nucleotides of algJ was removed. The deletion construct encodes an in-frame fusion of AlgI and AlgJ ensuring that AlgF and AlgA should be translated normally. A 3.4 kb SacI-XbaI DNA-fragment from pMG49 was then ligated into the suicide vector pHE55 digested with the same enzymes, creating pMG50. This plasmid, containing the sequences flanking the deletion, was introduced to Pf20118 by conjugation from $E.\ coli$ S17.1 and non-mucoid transconjugants were selected on PIA-medium with tetracycline. Transconjugant revertants were identified as mucoid tetracycline sensitive colonies on LA-medium. Four algIJΔ-mutant candidates were tested by PCR-amplification of a region containing the deleted region using the primer pair PfacetylFw and PfacetylRev (Table 2) and the PCR-product was analyzed by agarose gel electrophoresis. Two of the colonies contained the wild type fragment (1.8 kb) while the two others contained the mutant segment (0.4 kb). One of these was designated strain Pf20118algIJΔ. Pf20118algFΔ and Pf20118algIJΔ were grown in fermentors using the PM5-medium and standard growth conditions as set forth in Materials and Methods, and the produced alginate was harvested and measured as earlier described. The results are given in Table 4 below. Both variants produced mannuronan alginate in yields of 16-17 g alginate per liter medium. The presence of acetyl groups was determined by $^1$H-NMR-spectroscopy as described in Materials and Methods. Pf20118algFΔ did not produce acetylated alginate, while Pf20118algIJΔ produced alginate containing small amounts of O-acetyl groups.

TABLE 4

Alginate yield, fraction of guluronate residue content [$F_G$], degree of acetylation [da] and intrinsic viscosity [η] in fermentations with different $P.\ fluorescens$ mutants

| Mutant | Alginate (g/l) | $F_G$ (%) | da | η (dl/g) |
|---|---|---|---|---|
| Pf201 | 11.3 | 29 | 0.44 | 16.5 |
| Pf20118 | 16.0 | 0 | 0.60 | 17.3 |
| Pf20118 algIJΔ | 16.8 | 0 | 0.03 | 10.9 |
| Pf20118 algFΔ | 16.2 | 0 | 0 | 8.9 |

The fermentations were performed in 3-l fermentors using PM5-medium and standard growth conditions. Analyzes were done as described in Material and Methods.

Pf20118algFΔ and Pf20118algIJΔ are deposited in NCIMB under the accession numbers 41142 and 41143.

Example 5

Preparation of a Modified Derivative Mutant Strains Displaying Low Alginate Lyase Activity, Pf20118AlgLH203R.

$P.\ fluorescens$ has, according to current knowledge, only one alginate lyase (AlgL) encoded by the gene algL. An option for controlling the molecular weight of the alginate produced by this bacterium, is therefore to modify the AlgL gene product simultaneously produced.

The mutagenic primer pair algLH203R1/algLH203R2 was used to create a His203Arg (H203R) mutation in the algL gene of Pf20118. The primers also contain silent mutations creating an AgeI-site, for allele identification. The mutagenic plasmid pMG70 was constructed, as described in Table 1, and introduced to the Pf20118 chromosome by conjugation, and transconjugants were selected on PIA-medium with tetracycline and XGaI. Transconjugants were grown in series of over-night cultures in the absence of tetracycline and plated on PIA-medium with XGaI to isolate AlgL mutants. White tetracycline-sensitive mutant candidates were screened by PCR-amplification of the algL-allele using the primers PfalgL-BspHI-pMG26 and PfalgLRev1 (Table 2), and alleles were identified by digesting the PCR-fragment with AgeI. The mutant strain chosen was designated Pf20118AlgLH203R.

When the variant strain Pf20118AlgLH203R is grown in shake flasks using the PIA-medium with reduced salt it yields amounts of mannuronan, approximately at the same level as the variant strain Pf20118. Also growth in fermentor led to approximately the same amounts of mannuronan produced from the two variant strains (H203R produced 12 g mannuronan alginate per liter). The intrinsic viscosity measurements of the mannuronan produced by Pf20118 (intrinsic viscosity of 15 dl/g) and Pf20118AlgLH203R (intrinsic viscosity of 37 dl/g) in shake flasks (using PIA medium with reduced salt, no proteases were added) show that the latter produces a mannuronan with increased molecular weight. Pf201 produced alginate with an intrinsic viscosity like Pf20118 (15 dl/g).

Bacterial cells of Pf201, Pf20118 and Pf20118AlgLH203R were harvested at the end of the fermentation in shake flasks and sonicated. After sonication the extracts were investigated for alginate lyase activity, which was measured by the method as set out in Materials and methods. Defining the lyase activity of Pf201 as 100%, it is possible to detect activities down to 2% using this method. Pf20118 showed 93% activity. No activity was detected for Pf20118AlgLH203R, indicating that it is less than 2% of that of strain Pf201. Still, when the proteases Alkalase and Neutrase, both to 0.15 ml/l were added, the intrinsic viscosities increased to about 50 dl/g for Pf201 and Pf20118, and to 70 dl/g for Pf20118AlgLH203R, indicating that the mutant lyase has some residual activity. The variant strain Pf20118AlgLH203R is deposited in NCIMB under the accession number 41144.

Example 6

Preparation of Variant Mutant Strains with Reduced Epimerase Activity

The mutant strains Pf201 and Pf20118 provide the means to make alginate in vivo, with about 30% guluronate residue content and pure mannuronan, respectively. Alginates with intermediate amounts of guluronic acid (guluronate residue) content that is between 0 and 30% can however also be made. One way to obtain such strains is to delete the epimerase gene from the operon, and then introduce the gene controlled by a promoter either on a plasmid or a transposon. Plasmid pMG53 was constructed as described in Table 1, this plasmid contains a variant of algG in which the internal 40% of the gene has been removed. This plasmid was then transferred to Pf201 and a strain containing this deletion, designated Pf201ΔalgG, was made by homologous recombination. This strain did not make alginate, although it did make small oligouronides containing an unsaturated residue at the non-reducing end. Plasmid pCNB111 is a suicide plasmid, which contains a mini-transposon based on Tn5. Genes can be cloned into this mini-transposon in such a way that their expression is controlled by the inducible Pm-promoter. The wild-type algG-gene was transferred to this plasmid as described in Table 1, creating plasmid pKB10. The plasmid was conjugated into Pf201ΔalgG as described in the general description of Materials and Methods under homologous recombination. But incorporation in the chromosome was in this case dependent on the transposon, not on homology. The resulting strain was designated Pf201ΔalgG::TnKB10. This strain produces alginate even in the absence of inducer, but the amount of polymer increases with increasing concentration of inducer (not shown). When the product was analysed by NMR and by mass spectrometry it was found that the strain produces a mixture of alginate and oligomers. pKB10 was also transferred to Pf20118, creating strain Pf20118::TnKB10. This strain produces a mixture of wild-type alginate containing 30% G and mannuronan (results not shown). These results showed that not only is the epimerase necessary for alginate production, it also epimerizes as part of a protein complex. In order to obtain homogenous alginate, only one form of epimerase may be present.

A method for preparing variant strains with reduced epimerase activity is to exchange the wild type algG with a mutant gene encoding a mutant protein with reduced activity. It is now established a method for obtaining such mutants, using the properties of Pf201algG and pKB10. Exponentially growing cells ($OD_{600nm}$: 0.5) of *E. coli* S17.1 λ-pir (pKB10) were mutagenized by nitrosoguanidine. Cells from 5 ml culture were washed twice in 5 ml TM-buffer (1.0 g/l $(NH_4)_2SO_4$, 0.1 g/l $MgSO_4 \times 7H_2O$, 5 mg/l $Ca(NO_3)_2$, 0.25 mg/l $FeSO_4 \times 7H_2O$, 5.8 g/l maleic acid, 6.05 g/l Tris, pH adjusted to 6.0 with NaOH). The cells were re suspended in 2.85 ml TM-buffer and treated with 100 μg/ml nitrosoguanidin for 37° C. for 30 min. The suspension were cooled on ice for three minutes, the cells were pelleted by centrifugation and washed three times in 5 ml LB. Glycerol was added to a final concentration of 10%, and the re suspension was frozen at −80° C. Only 0.007% of the cells survived the mutagenesis. The plasmids were isolated from the thawed cells and transformed into *E. coli* S17.1 μ-pir, of table 1. The plasmids were now designated pKB10-M* to emphasise that they constitute a library of mutated versions of pKB10.

pKB10-M* was then conjugated into *P. fluorescens* Pf201ΔalgG as described in the Materials and Methods section (under "homologous recombination") except that 100 μl frozen *E. coli* μ-pir (pKB10-M*) was inoculated directly into 10 ml LB-medium and grown for 2 hours before being mixed with the *P. fluorescens* strain. $OD_{600\ nm}$ of both cultures were 0.4. After incubation on LA-medium at 30° C. for 36 hours the conjugation mixture was plated on PIA-medium (Difco) containing 40 μg/ml kanamycin (Km). Only those *P. fluorescens* cells in which the transposon TnKB10-M* has integrated into the chromosome will grow on this medium, because pKB10 and its derivatives are unable to replicate in *P. fluorescens*. Even in the absence of inducer some AlgG is expressed from the Pm-promoter in *P. fluorescens* and this level is sufficient to give mucoid colonies in strain Pf201ΔalgG::TnKB10. About 0.5% of the colonies were non-mucoid indicating either that the algG gene in these cells was not expressed due to mutations in either the Pm-promoter or in the mRNA-leader sequence or that the AlgG protein is non-functional.

Each plate (245×245 mm) contained 4-5000 colonies, and between 1200 and 1400 of these could be picked from each plate using an automated colony-picker, Genetix Q-pixII, Genetix Limited, UK. The parameters were adjusted such that the small (non-mucoid) colonies were not picked. A method for screening the strain containing the mutated library was developed. In this screen the parameters cell growth, alginate production (measured using a mixture of M- and G-lyases), and G-content (measured by using G-lyases only), respectively were measured;

Growth of Bacteria

The colonies were replicated to two different liquid media in 96 well plates using a Genetix Q-pixII colony picker. To preserve the clones one replica was grown in 110 μl LB-medium containing triclosan (0.025 g/l) and kanamycin (Km) (40 mg/l) and incubated for 48 hours at 25° C. Glycerol (60%, 40 μl) was added to each well, the solutions were mixed, and the plates were frozen at −80° C.

The other replicas were grown in 0.5×PIA (bacteriological pepton (10 g/l), NaCl (2 g/l), $MgCl_2$ (0.7 g/l), $K_2SO_4$ (5 g/l), glycerol (5 g/l), triclosan (0.025 g/l) and Km (40 mg/l).) m-toluate (inducer) was added to 0.1 mM. The bacteria were grown in sterile Nunc 96-V-well plates containing 110 μl medium/well, and incubated for 72 hours at 25° C. using 900 rpm, orbital movement 3 mm amplitude.

Measurement of Alginate Production

NaCl (0.2 M, 120 μl) was added to each well, and the cells were pelleted by centrifugation (3900 g, 20° C., 30 min). 50 μl supernatant from each well were transferred to a Nunc 96-flatwell plate. The alginate was deacetylated by adding NaOH (0.6M, 10 μl) to each well, mixing for 25 seconds, and incubating at room temperature for 1 hour. 100 μl lyase reaction buffer (50 mM Tris-HCl, 1.5% NaCl (pH 7.5)) was then added, and the solutions were mixed for 60 seconds.

75 μl from each well was transferred to a Costar-UV 96-well plate. Another 150 μl lyase reaction buffer was added, and the solutions were mixed for 25 seconds. The absorbance at 230 nm (A1) was read, then 8 μl of G-specific alginate lyase (0.2 u/ml) was added to each well. The solutions were mixed for 25 seconds, and incubated at room temperature for 60 min. They were again mixed for 25 seconds, and read at A230 nm (A2). Then 8 μl of M-specific alginate lyase (1 u/ml) were added to each well, the solutions were mixed for 25 seconds and incubated at room temperature for 60 minutes. The solutions were again mixed for 25 seconds and read at A230 nm (A3). The absorbance, of the added lyases was subtracted from the readings of A2 and A3. Alginates of known composition (polymannuronic acid produced by Pf20118 and alginate with a G-content of 30% produced by Pf201) were used as standards in the assays.

The total amount of alginate is calculated based on the formula:

$$A_{alg} = A3 - A1$$

By comparing $A_{alg}$ from the samples with $A_{alg}$ from standards with known alginate concentration, the alginate concentration in the samples is calculated.

Measurement of Guluronic Acid (G) Content

The relative G-content ($G_r$) in a sample is calculated by the formula $$G_r = (A2 - A1)/(A3 - A1)$$

By comparing the $G_r$ from the samples with $G_r$ of the standards the G-content in the sample was calculated.

Ten thousand colonies were screened in this way, and a few candidates with altered, but not zero, activity were picked. These mutants were then grown in shake flasks, as described under Materials and Methods. The PIA-medium used was added triclosan (0.025 g/l), kanamycin (40 mg/l) and m-toluate (0.1 mM), and the alginate produced was analysed by NMR as described in the Materials and Methods section. One mutant produced alginate containing only 13% guluronic acid residues, whereas the wild-type produces alginate containing about 30% guluronic acid residues (Table 4). Some other strains producing pure mannuronan were also found. The method makes it possible to screen mutant forms of AlgG that introduces less guluronic acid than the wild-type enzyme.

In order to produce further variant mutant strains producing a desired alginate product, the mutant genes may be recovered using known PCR techniques, cloned into pMG48, and transferred into Pf201 or actually any of the overproducing strains using homologous recombination, as previously described in the description. Similar to the mannuronan-producing strains; Pf2012, Pf2013, Pf20118, and Pf20137, a point mutation in algG affecting the epimerization is not likely to affect the amount of alginate produced.

Example 7

Preparation of Variant Mutant Strains with Reduced Epimerase Activity

An alternative method for preparing variant strains with reduced epimerase activity is to exchange wild type algG with a mutant gene encoding a mutant protein with less activity. Four different amino acid substitutions are shown in Table 3 to give epimerase negative mutants of AlgG. In these four cases the amino acid change affect either the size or the charge of the amino acid, for two of them both properties are changed. Possible additional amino acids can also be identified by sequencing mutants found by the method described in example 6. Alternative alleles of algG encoding more conservative changes in these amino acids is made by site specific mutagenesis using pMG26 as template. Mutagenic primers are made which contain a codon for the new amino acid flanked by about 10-15 nucleotides identical to the known sequence. Mutations in Ser337 will destroy the SmaI site, primers for the other amino acids do preferably contain silent mutations introducing a restriction enzyme site to aid in identifying the new mutant strains. Primers for both strands are to be synthesized, and the mutagenesis is performed as described in Material and Methods. Mutated algG-alleles are then transferred to pMG48 digested with NsiI-NcoI as a 2.7 kb BspHI-PstI-digested DNA fragment. The resulting plasmids are transferred to Pf201 and transconjugants selected as being non-mucoid, tetracycline resistant, and blue on agar plates containing XGaI. After growing selected clones for several successive transfers in LB-medium, double recombinants are selected as having white, mucoid colonies on agar plates containing XGaI, and by being sensitive to tetracycline. algG from these candidates can be amplified using the primer pair PfalgG5f and PfalgG3r. The amplified product is 1.7 kb long. If a restriction site is removed, or introduced by the primers, the correct mutants are identified by using the corresponding restriction enzyme. Alternatively the candidates are confirmed by DNA-sequencing.

The mutant strains are grown in shake flasks, and the alginate produced is isolated as described in Materials and Methods. The amount of alginate and the G-content are determined using M- and G-lyases as described in Materials and Methods. The results from interesting strains are verified by NMR-spectroscopy.

Example 8

Preparation of Variant Mutant Strain Pf201MC with an Inducible Pm Promoter for Regulation of the Alginate Production The Pm promoter together with its effector protein XylS is known to be a strong inducible promoter which can be used in many gram-negative species, Blatny et al., 1997, 63, Appl. Environ. Microbiol. p. 370-379. The inducer used is often toluate, which diffuses freely over the bacterial membranes. The *P. fluorescens* strain Pf0-1 has now been sequenced at JGI (The DOE Joint Genome Institute) (http://spider.jgipsf.org/JGI microbial/html/pseudomonas/pseudo homepage.html). When the alginate operon of this strain was compared to known alginate operon sequences from other *Pseudomonas* species, we found that the organization was similar. All sequenced alginate-producing species of *Pseudomonas* also have the same conserved open reading frame upstream of the alginate promoter. It potentially encodes a protein, the function of which is unknown. The objective of this experiment was to exchange the sequences downstream of the stop codon for this reading frame and upstream of the start codon of algD, the first gene in the alginate operon, with sequences encoding XylS, the Pm-promoter and the Shine-Dalgarno sequence from the vector pJB658 described in Blatny et al., 1997, 38, p. 35-51. Most of the DNA-segment, which separates xylS and the Pm-promoter in pJB658, was removed.

Figure 5:
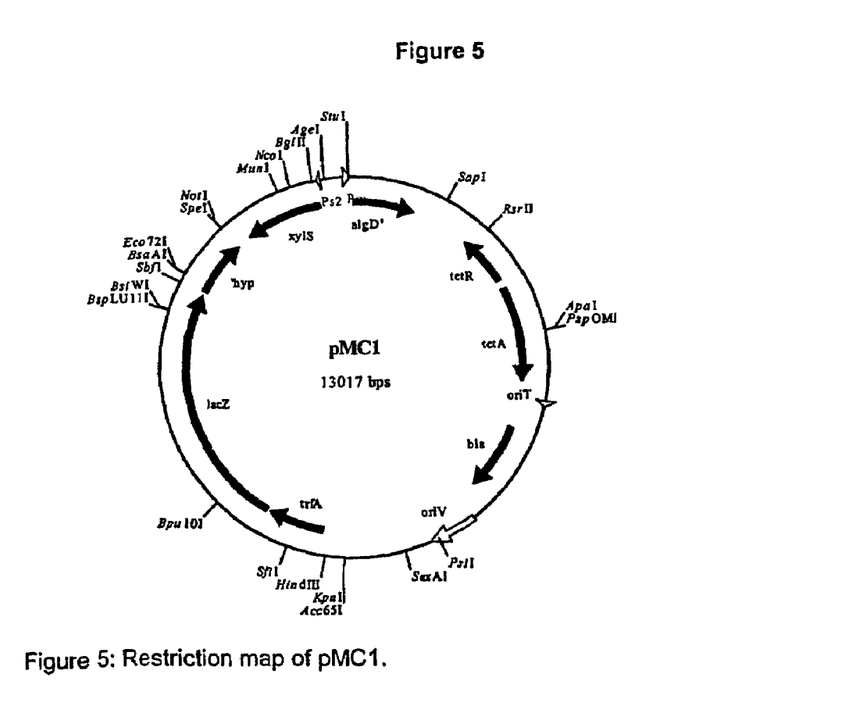
FIG. 5: Restriction endonuclease map of the plasmid pMC1. Only unique restriction enzymes are shown.

The first step was to clone the 3' part of the hypothetical protein (abbreviated hyp) and the 5' part of algD in order to get flanking sequences for the insertion. When the sequences of algEGXLIJFA of strain Pf0-1 were compared to the sequences of NCIMB10525, it was found that the two sequences were not identical. The primers were therefore constructed using parts of the hyp and algD genes, which are highly conserved in several species. The 3' part of hyp was cloned as a 0.7 kb BspLU11I-SpeI-digested PCR fragment using the primers HypBspLU11I and HypSpeI of Table 2, into the suicide vector pMG48, generating pHE139. The 5' part of algD was cloned as a 0.8 kb NdeI-NsiI restricted PCR-fragment into NdeI-PstI-restricted pJB658celB, generating pHE138. The replacement vector pMC1, confer FIG. 5 was then constructed through a series of cloning steps (Table 1).

The plasmid was transferred by conjugation to strain Pf201 as described in Materials and Methods, choosing XGaI and tetracycline resistance/sensitivity to screen for recombinants and subsequent double recombinants. Colonies, which seemed to be more mucoid on PIA-medium containing 1 mM toluate, than on PIA-medium not containing toluate, were chosen for further analyses by PCR. Using the primer pair HypBspLU11I and AlgDNsiI (Table 2) the expected PCR-product from wild type strains would be 2.3 kb long, while that of the mutant strain would be 3.0 kb. The chosen mutant was designated Pf201MC. This strain was then fermented in the absence and presence of toluate (0.025 mM) as an inducer. PM5-medium and standard conditions were used during the fermentation, as described in Material and Methods. The un-induced culture produced 3.5 g alginate per liter medium, whereas the induced culture produced 13 g alginate per liter medium. The mutant strain Pf201MC is deposited in NCIMB under the accession number 41145.

Example 9

Use of an Inducible Mutated Pm Promoter for Regulation of Alginate Production

The wild type Pm-promoter does function, however the un-induced level of expression is fairly high. It has been developed a method to screen for mutations in the said promoter, based on the work of Winther-Larsen et al., Metabol. Eng. (2000), 2, p 92-103. The original pJT19-bla was changed by inserting a terminator sequence and an AflIII-site upstream of the Pm-promoter and the SpeI-site downstream of the promoter was changed into a BspLU11I-site. The new plasmid was designated pIB11. In this plasmid the Pm-promoter is flanked by unique XbaI and BspLU11I restriction sites. Two complementary 50 bp DNA-oligomers covering this DNA-fragment were then synthesised. The conditions were chosen to give an error rate of about 12% over the nucleotides flanked by these restriction sites. The corresponding wild-type strands were also synthesised. A library of double-stranded oligonucleotides was then made by annealing each of the oligonucleotides containing mutations with the complementary wild-type oligonucleotide. The ends of the oligonucleotides were constructed to be complementary to pIB11 restricted with XbaI and BspLU11I. The annealed oligonucleotides were then ligated into pIB11 restricted with XbaI and BspLU11I, and 50 000 transformants were obtained. In $E.$ $coli$ this library might be screened using resistance for ampicillin as a marker. But $P.$ $fluorescens$ already has a fairly high resistance towards β-lactams. The gene for β-lactamase was exchanged with a gene encoding luciferase as described in Table 1, creating the vectors pHH100 containing the wild-type-promoter and pHH100-library containing the library of promoters. The pHH100-library contains 8000 independent transformants. It was then transferred to $P.$ $fluorescens$ by conjugation as described in Materials and Methods.

The library of mutated Pm-promoters was screened for luciferase activity using the assay described by Wood, K. V. and DeLuca, M. (1987, Anal. Biochem. 161: 501-507). To obtain reproducible results we found that the bacteria first had to be grown in microtiter plates containing 110 μl liquid PIA-medium with 40 μg/ml kanamycin (Km) (25° C., 48 hours, shaking at 900 rpm). Some bacteria were then diluted in new medium, using a sterile stamp for transfer, and then stamped onto two nylon filters. The filters were placed on PIA-plates with and without inducer (1 mM m-toluate), the bacteria facing up, and incubated for 14 hours at 30° C. The filter was then placed in a Petri dish containing 3 ml luciferin (Promega), (1 mM in 0.1 M sodium citrate, pH 5.0), shaken until the liquid was distributed evenly, and incubated for 10 minutes. It was placed on a filter-paper to remove the liquid, and placed, face down, on transparent plastic film. A dry filter paper was placed on top of it to remove residual dampness. The nylon filter was then exposed for 10 min. using a Kodak 2000IR camera. 1200 colonies were screened by this method, and 84 were identified that showed no or only weak activity from colonies grown without inducer and readily detectable activity from colonies grown in the presence of inducer. Seventy-nine of these colonies were re-screened, and seventy-five of them showed significantly lower activity in the absence of inducer compared to the wild-type pHH100.

Six of these clones were grown in 10 ml LB containing 50 mg/l kanamycin. Five were chosen because their expression levels without inducer was very low, the sixth (Pf201 (pHH100-E1)) had an intermediary level of expression without added inducer, but also a significantly higher expression level in the presence of inducer. Stationary phase cultures (100 μl) were then transferred to two shake flasks containing 10 ml fresh LB-medium and incubated for two hours before adding m-toluate to a final concentration of 1 mM. The cultures were harvested 14 hours after induction. Ninety μl culture were then added to 1.5 ml tubes containing 10 μl buffer (1 M $K_2HPO_4$, 20 mM EDTA, pH 7.8) and frozen at −80° C. Luciferase activity was measured using the Luciferase assay system from Promega Inc (Cat. nr. E1500) (Table 5). The method proved to be useful to find mutant promoters achieving not only a very low un-induced expression level, but also having a low un-induced expression level and still a fairly high induced expression level compared to the wild type. The results are given in the table below.

TABLE 5

| Luciferase activities from Pm expression in $P.$ $fluorescens$-mutants | | | | | |
|---|---|---|---|---|---|
| | Uninduced cells | | Induced cells | | |
| Clone | Activity$^a$ | %$^b$ | Activity$^a$ | %$^b$ | Ratio$^c$ |
| NCIMB10525 (pHH100) | 11.6 | 100 | 605 | 100 | 52 |
| NCIMB10525 (pHH100-A2) | 0.7 | 6.0 | 3.2 | 0.5 | 5 |
| NCIMB10525 (pHH100-B1) | 1.3 | 11 | 5.7 | 0.9 | 4 |
| NCIMB10525 (pHH100-D6) | 1.2 | 11 | 15 | 2.4 | 12 |
| NCIMB10525 (pHH100-D9) | 0.5 | 4.2 | 8.7 | 1.4 | 18 |
| NCIMB10525 (pHH100-E1) | 7.8 | 67 | 1050 | 173 | 134 |
| NCIMB10525 (pHH100-G5) | 0.5 | 4.3 | 69 | 11.4 | 138 |

Strain NCIMB10525 was used as blank, and had no measurable activity. The average results from two independent inoculations of each strain are shown.
$^a$The activity is given in arbitrary units (the values are dependent on the settings of the instrument).
$^b$Activity in percent of percent of wild-type levels.
$^c$Induced/uninduced values.

Example 10

In vitro Epimerization of Mannuronan Alginate Product

Mannuronan produced as described in example 4, was dissolved in buffer (Mops (50 mM), $CaCl_2$ (2.5 mM), NaCl (10 mM), pH 6.9) to a concentration of 0.25% mannuronan alginate. The mannuronan C5-epimerase AlgE4 produced and purified as described by Ramstad et al, Enzyme and Microbial Technology, (1999), 24, p 636-646, was added to a concentration of 1 mg enzyme/200 mg mannuronan. The solution was incubated at 37° C. for 23 hours. The epimerization was stopped by acid precipitation of the alginate. The alginate was then re-dissolved in distilled water and neutralized with alkali. The alginate solution was added NaCl to a concentration of 0.2% and one volume of ethanol (96%) to precipitate the alginate. The precipitated alginate was washed 3 times with 70% ethanol, and 2 times with 96% ethanol, and freeze dried. The freeze-dried alginate was treated further and analyzed by NMR as described in Materials and Methods. The product after this incubation was an almost totally poly alternating alginate (PolyMG, Table 6).

Poly MG was re-dissolved in buffer (Mops (50 mM), $CaCl_2$ (2.5 mM), NaCl (10 M), pH 6.9). The mannuronan C5-epimerase AlgE1 was produced and purified as described by Ramstad et al, Enzyme and Microbial Technology, (1999), 24, p 636-646, except that it was purified by ion-exchange chromatography only. It was added to a concentration of 1 mg enzyme/200 mg mannuronan. The solution was incubated at 37° C. for 4 days. Additional AlgE1 (1 mg enzyme/200 mg mannuronan) was added after 1, 2 and 3 days incubation. The epimerization was stopped as described above. Alginate was isolated and analyzed by NMR as described above. The result of the epimerization was an alginate with a G-content of >95% (Table 6).

TABLE 6

Composition of alginate after epimerization of mannuronan with AlgE4 and AlgE1

| Alginate | FG | FM | FGG | FGM/MG | FMM |
|---|---|---|---|---|---|
| Mannuronan | 0 | 1.0 | 0 | 0 | 1.0 |
| PolyMG (mannuronan + AlgE4) | 0.45 | 0.55 | 0 | 0.45 | 0.1 |
| Poly G (PolyMG + AlgE1) | >0.95 | <0.05 | >0.9 | <0.05 | <0.02 |

Example 11

Alginate Production Utilizing Different Carbon Sources

*Pseudomonades* are known to have the ability to utilize numerous compounds for growth. In this example the ability of metabolising different carbon sources to alginate is demonstrated using the PM5-medium replacing fructose with the actual carbon source. The medium composition, growth conditions and analyses of alginate concentrations in these fermentation experiments were performed as described in "General description of Materials and Methods", unless otherwise stated.

The ability to produce alginate is demonstrated for an alcohol (glycerol), monosaccharides (fructose, glucose) and for a disaccharide (lactose) (see Table 7).

*P. fluorescens* does not encode β-galactosidase, and is therefore unable to use lactose as a carbon source even though it can grow on both glucose and galactose. We transferred the plasmid pHM2 encoding *E. coli* β-galactosidase (LacZ) and lactose permase (LacY), as described by Mostafa, H. E., Heller, K. J., Geis, A. 2002. Appl. Environment. Microbiol. 68: 2619-2623, to strain Pf201 by conjugation as described in the chapter of homologous recombination in the description. The resulting strain is denominated Pf201(pHM2). To avoid problems of plasmid loss, lacZ and lacY could preferably be inserted into the chromosome using derivatives of plasmid pCNB111. Whey, a waste product from the production of cheese, contains high amounts of lactose. When Pf201 (pHM2) was grown in PM5medium containing 27.5% ultrafiltrated whey, corresponding to 50.9 g/l lactose in the medium, 13.3 g/l alginate was produced.

The results obtained are given in table 7 and indicate that numerous carbon sources can be utilized to yield large amounts of alginate by the alginate overproducing mutant strains.

TABLE 7

Production of alginate by utilization of different carbon sources (C-source)

| Strain | C-source | Amount of C-source (g/l) | Volumetric yield of alginate (g/l) | C-yield (g alginate/g C-source) |
|---|---|---|---|---|
| Pf20118 | Fructose[1] | 40 | 16.0 | 0.40 |
| Pf20118 | Glucose[2] | 40 | 13.0 | 0.33 |

TABLE 7-continued

Production of alginate by utilization of different carbon sources (C-source)

| Strain | C-source | Amount of C-source (g/l) | Volumetric yield of alginate (g/l) | C-yield (g alginate/g C-source) |
|---|---|---|---|---|
| Pf20118 | Glycerol[1] | 40 | 17.1 | 0.43 |
| Pf201(pHM2) | Lactose[3] | 51 | 13.3 | 0.26 |

[1] All of the carbon source (40 g/l) is added before inoculation of the fermentation.
[2] 4.5 g/l glucose is added to the medium before the start of the fermentation. The rest of the glucose (35.5 g/l) is fed at a continuous rate (1 g glucose/liter, hour). The glucose-feeding is started 10 hours after inoculation
[3] Ultrafiltrated whey containing as main compound lactose and minerals as minor compounds are added to the PM-5 medium. The ultrafiltrated whey also contains traces of milk proteins. The lactose concentration in the medium was 51 g/l after the addition of the ultrafiltrated whey. The ultrafiltrated whey was added before inoculation of the fermentations.

The invention claimed is:

1. A mutant strain of *P. fluorescens* selected from the group consisting of the mutant strain Pf201, Pf2012, Pf2013, Pf20118, Pf20137, Pf20118alglJΔ, Pf20118algFΔ, Pf20118AlgLH203R and Pf201MC.

2. The mutant strain of *P. fluorescens* of claim 1, wherein the said mutant strain is selected from the group consisting of: Pf2012, Pf2013, Pf20118, and Pf20137.

3. The mutant strain of *P. fluorescens* of claim 1, wherein the said mutant strain is selected from the group consisting of: Pf20118alglJΔ and Pf20118algfΔ.

4. The mutant strain of *P. fluorescens* of claim 1, wherein the said mutant strain is Pf20118AlgLH203R.

5. The mutant strain of *P. fluorescens* of claim 1, wherein the said mutant strain is Pf201MC.

6. A mutant strain of *P. fluorescens* Pf201, wherein said mutant strain produces at least 10 g alginate per liter medium and is stable over at least 60 generations.

7. The mutant *P. fluorescens* strain of claim 6 which has a mutation corresponding to the mutation in strain Pf201 which results in alginate production at the level of at least 10 g alginate per liter medium.

8. The mutant strain of *P. fluorescens* of claim 6, wherein said mutant strain produces at least 10 g alginate per 40-55 g carbon source per liter medium.

9. The mutant strain of *P. fluorescens* of claim 6, wherein said mutant strain produces at least 10 g alginate per 50-55 g carbon source per liter medium.

10. The mutant strain of *P. fluorescens* of claim 6, wherein said mutant strain produces at least 10 g alginate per 40 g carbon source per liter.

11. The mutant strain of *P. fluorescens* of claim 6, wherein the said mutant produces an alginate consisting of mannuronate residues only.

12. The mutant strain of *P. fluorescens* of claim 6, wherein the said mutant produces alginate having a defined guluronate residue (G)-content between 0 and 30%.

13. The mutant strain of *P. fluorescens* of claim 6, wherein the said mutant produces alginate without, or with a reduced number of O-acetyl groups.

14. The mutant strain of *P. fluorescens* of claim 6, wherein the said mutant produces alginate with a molecular weight of between 50,000 and 3,000,000 Daltons.

15. The mutant strain of *P. fluorescens* of claim 6, wherein the mutant strain further comprises a mutant gene selected from the group consisting: a mutant algG gene, a mutant algI gene, a mutant algJ gene, a mutant algL gene, and a mutant algF gene.

16. The mutant strain of *P. fluorescens* of claim 6, wherein the mutant strain further comprises a mutant algG gene which encodes an epimerase enzyme having reduced epimerase activity.

17. The mutant strain of *P. fluorescens* of claim 6, wherein the mutant strain further comprises a mutant algG gene which is inactivated.

18. A biologically pure bacterial culture of the mutant strain of *P. fluorescens* of claim 6.

* * * * *